United States Patent [19]
Chen et al.

[11] Patent Number: 5,728,878
[45] Date of Patent: Mar. 17, 1998

[54] FUNCTIONAL N-VINYLFORMAMIDES

[75] Inventors: Ning Chen, Allentown; Walter Louis Renz, Macungie; Robert Krantz Pinschmidt, Jr., Allentown; William Eamon Carroll, Orefield, all of Pa.

[73] Assignee: Air Products and Chemicals, Inc., Allentown, Pa.

[21] Appl. No.: 674,412

[22] Filed: Jul. 2, 1996

[51] Int. Cl.$^6$ .................................................. C07C 233/03
[52] U.S. Cl. ........................... 564/159; 564/152; 564/153
[58] Field of Search ........................... 564/153, 159, 564/152

[56] References Cited

U.S. PATENT DOCUMENTS

| | | | |
|---|---|---|---|
| 4,064,026 | 12/1977 | Kaufman | 204/159.19 |
| 4,126,527 | 11/1978 | Kaufman | 204/159.22 |
| 4,129,709 | 12/1978 | Lorenz et al. | 526/264 |
| 4,205,139 | 5/1980 | Barzynski et al. | 525/38 |
| 4,284,776 | 8/1981 | Gruber et al. | 544/400 |
| 4,319,811 | 3/1982 | Tu et al. | 351/166 |
| 4,348,427 | 9/1982 | Priola et al. | 427/44 |
| 4,424,314 | 1/1984 | Barzynski et al. | 525/454 |
| 4,725,524 | 2/1988 | Elzer et al. | 430/258 |
| 5,281,682 | 1/1994 | Cornforth et al. | 526/273 |
| 5,463,110 | 10/1995 | Chen et al. | 560/172 |

*Primary Examiner*—Shailendra Kumar
*Attorney, Agent, or Firm*—Mark L. Rodgers

[57] ABSTRACT

N-vinyl compositions comprising 3-(N-vinylformamido) propionamides and 2-methyl-3-(N-vinylformamido) propionamides containing terminal amino, hydroxyl or a second N-vinyl group are obtained by amidation of the corresponding propionate ester with appropriate alkylamines. The invention also describes a process for preparing these compounds. The subject materials are useful as monomers in free radical polymerization as well as precursors in the preparation of unsaturated resins.

10 Claims, No Drawings

FUNCTIONAL N-VINYLFORMAMIDES

TECHNICAL FIELD OF THE INVENTION

The present invention discloses N-vinyl compositions comprising 3-(N-vinylformamido)-propionamides and 2-methyl-3-(N-vinylformamido)propionamides which optionally contain terminal amine, hydroxyl or a second N-vinyl group. The invention also describes a process for preparing the same. These materials are useful as monomers in free radical polymerization as well as precursors in the preparation of unsaturated resins.

BACKGROUND OF THE INVENTION

The most commercially important class of radiation-curable compositions relies upon the free radical photopolymerization of acrylic compounds. These systems are commonly based on acrylic ester-terminated oligomers derived from one of several major resin chemistries, such as urethanes, epoxies or polyesters. The acrylated oligomers are often compounded with various nonpolymerizable materials (pigments, fillers, flow agents, antioxidants, etc), as well as photoinitiators and co-catalysts, and applied to a substrate before curing. Curing is accomplished by exposing the formulation to ultraviolet light or other type of radiation until a dry adherent polymerized film is formed. Formulations of this general description find use as printing inks, protective coatings, adhesives and the like.

In practice, it is often necessary to incorporate diluent monomers into these formulations in order to lower the viscosity of the oligomers sufficiently to permit adequate flow and leveling on the substrate prior to irradiation. This is particularly true of formulations applied by methods common to the printing and coating industries. Diluent monomers used for this purpose fall into two broad catagories: multifunctional (polyunsaturated) types and monofunctional (monounsaturated) compounds. Multifunctional acrylate monomers generally provide high cure speed and high crosslink density, leading to hard, chemically-resistant films, but they may not sufficiently lower viscosity and may cause excessive film brittleness or contribute to poor adhesion due to excessive shrinkage of the films on curing. Monofunctional monomers are usually more effective in reducing viscosity, and can yield softer, more extensible films that exhibit better adhesion to many substrates.

Lorenz et al. (U.S. Pat. No. 4,129,709) disclose a coating composition comprising N-vinyl-2-pyrrolidone, an acrylated oligomer, and an acrylic acid ester having a boiling point of at least 200° C. at 760 mm Hg. These compositions may be cured by exposure to actinic radiation between 200 and 750 nm or by an electron beam. Tu et al. (U.S. Pat. No. 4,319,811) describe radiation curable coatings consisting of triacrylate or tetraacrylate monomers with an N-vinyl imido monomer, preferably an N-vinyllactam such as N-vinyl-2-pyrrolidone. Priola and coworkers (U.S. Pat. No. 4,348,427) describe compositions comprising mixtures of acrylated oligomers and/or unsaturated polyester oligomers with a least one unsaturated compound of the amide, lactam, piperidone and urea classes, and curing them by exposure to ultraviolet radiation in the 200-400 nm range. Cornforth et al. (U.S. Pat. No. 5,281,682) teach improved radiation-curable formulations containing N-vinylformamide and an oligomer selected from the group epoxy acrylates, urethane acrylates, polyester acrylates and mixtures thereof. Elzer et al. (U.S. Pat. No. 4,725,524) disclose a dry film photoresist containing an acrylic or methacrylic oligomer, a compatible film-forming water-soluble polymer, one or more compatible photopolymerizable monomers, a photoinitiator, and other additives. In U.S. Pat. No. 4,284,776 Gruber et al. disclose radiation curable acrylyloxy monomers obtained by the Michael addition of an amide acrylate material with a primary or secondary amine. Barzynski et al. (U.S. Pat. Nos. 4,205,139 and 4,424,314) teach curable compositions containing N-vinyl compounds in which at least two N-vinyl groups are present and in which at least one carbonyl group is bound to the nitrogen of the N-vinyl group, said carbonyl group in turn being bonded to a nitrogen or carbon atom.

Chen et al. in U.S. Pat. No. 5,463,110 and copending application Ser. Nos. 08/527,311, 08/489,889 and 08/572,416 teach preparation and uses of monounsaturated and polyunsaturated N-vinyl compounds obtained by the Michael addition reaction of N-vinylformamide with acrylic acid esters. The resulting alkyl 3-(N-vinylformamido) propionate esters exhibit low toxicity and have been found to be useful as monomers in polymerization processes, including as components of radiation-curable coatings.

(Meth)acrylic esters and (meth)acrylamides containing hydroxy or amino functionality are well known in the art. Aminoalkyl acrylate esters, typically in their tertiary or quaternary amine form (e.g. dimethylaminoethyl acrylate and the methyl chloride quaternary salt of dimethylaminoethyl acrylate) are frequently employed as comonomers in synthesis of cationic water-soluble polymers. Primary and secondary aminoalkyl acrylates are much less common and tend to be unstable in their unprotonated form due to the propensity for intra- and intermolecular reactions of the basic amine.

Hydroxy-functional acrylic esters, principally 2-hydroxyethyl acrylate (2-HEA), have been suggested as diluent monomers in radiation curing and are widely employed as functional comonomers in conventional polymer synthesis where they facilitate the preparation of acrylic resins containing reactive hydroxyl groups. Such resins are employed, for example, in thermosetting coatings such as powder coatings and automotive finishes where they can be cured by reaction with melamine resins, polyisocyanates and epoxides. Owing to the vapor and dermal toxicity of 2-HEA, however, use of the monomer in radiation curing has been largely confined to the preparation of unsaturated urethane resins where, in one synthetic approach, 2-HEA is reacted with an isocyanate-terminated prepolymer to yield a photocurable resin (e.g., U.S. Pat. Nos. 4,064,026 and 4,126,527). In order to minimize the health risks associated with handling these materials, the levels of residual 2-HEA in these resins, as well as in formulated radcure coatings, must be maintained at low levels.

Copending application Ser. No. 08/323,210, discloses a technique for replacing hydroxyalkyl acrylates in the preparation of curable urethane resins by reacting a secondary N-vinylamide monomer, such as N-vinylformamide, with a polyisocyanate monomer which is subsequently reacted with at least one mono- or polyhydric alcohol to form a urethane linkage. The resulting N-vinyl-N-acyl oligomers contain no residual hydroxyacrylate monomer and are curable by ultraviolet radiation. However, preparation of these resins may be difficult due to poor selectivity and/or low reactivity of the amide hydrogen with certain diisocyanates.

In principle, it would be useful to have N-vinyl compounds analogous to those described in U.S. Pat. No. 5,463,110 that additionally possess reactive primary or secondary amino, or hydroxyl functionality. Unfortunately, routes to hydroxyalkyl and aminoalkyl 3-(N- vinylformamido)propionate monomers have proven unexpectedly elusive. As disclosed in Ser. No. 08/527,311, the preferred Michael acceptors for reaction with N-vinylformamide are (meth)acrylate esters that do not contain a source of active hydrogen in their structure (e.g. hydroxyl or primary amine groups). Thus, it is found that the attempted Michael reaction of N-vinylformamide with 2-hydroxyethyl acrylate gives little or no conversion to the desired 2-hydroxyethyl 3-(N-vinylformamido)-propionate, even under severe conditions.

Alternative routes to hydroxyalkyl and aminoalkyl 3-(N-vinylformamido)propionate monomers via postreactions at the ester linkage of alkyl 3-(N-vinylformamido)-propionates have proven suprisingly ineffective. Transesterfication, proposed in U.S. Pat. No. 5,463,110, has been found to be generally unproductive. For example, the attempted reaction of alkyl 3-(N-vinylformamido)propionates with diols such as ethylene glycol gives little conversion to the hydroxyalkyl 3-(N-vinylformamido)propionate ester using conventional catalysts under conditions sufficiently mild to preserve the vinyl bond.

Amidation of 3-(N-vinylformamido)propionate monomers is more successful although not universally effective since many common amines also show unexpectedly poor reactivity with these monomers. As the present invention discloses, however, amines of a particular structure exhibit acceptably high reactivity with 3-(N-vinylformamido)-propionate esters under relatively mild conditions. By proper selection of one of these coreactants, functional 3-(N-vinylformamido)propionamide monomers can be obtained in high yield in a practical process.

It is the object of this invention to provide unique 3-(N-vinylformamido)propionamide monomers that contain terminal functionality, in particular, amine, hydroxyl or a second N-vinyl group, and a process for preparing the same. The materials of this invention are expected to have general utility in organic synthesis and a wide array of free radical polymerization reactions, for example as diluent or crosslinking monomers in UV-curable coatings and inks; as raw materials for the preparation of unsaturated resins; and as functional comonomers in emulsion, bulk, suspension, and solution polymerization.

SUMMARY OF THE INVENTION

The present invention relates to unsaturated monomers comprising the 3-(N-vinyl-formamido)propionamides and 2-methyl-3-(N-vinylformamido)propionamides obtained from the reaction of a 3-(N-vinylformamido)propionate or 2-methyl-3-(N-vinyl-formamido)propionate ester and an amine.

Reaction of esters with amines to prepare amides is a well-known reaction, but one that typically requires strong base catalysts and elevated temperatures, temperatures which would be expected to hydrolyze or decompose 3-(N-vinylformamido)propionates. Unexpectedly, the subject compounds are readily prepared by the nucleophilic reaction of certain functional amines with a 3-(N-vinylformamido) propionate or 2-methyl-3-(N-vinylformamido)propionate ester under mild conditions in the presence of a trace quantity of basic catalyst such as sodium methoxide. The reaction temperature ranges from about 20° to 170° C. and the reaction is complete in between about 5 and 180 minutes. The alcohol coproduct from the reaction can be readily removed, for example by distillation at reduced pressure on a rotary evaporator.

The compounds of this invention are suitable for a large number of uses in polymerization and organic synthesis. For example, the materials may be employed as reactive diluents or crosslinking monomers in radiation-curable formulations. Additionally, the compounds may be useful as alternatives to hydroxyalkyl acrylates in the preparation of unsaturated urethane resins. Finally, the subject compounds could prove useful in conventional polymer synthesis (e.g. emulsion, solution, bulk or suspension polymerization) for the preparation of homopolymers, or as functional comonomers in combination with other ethylenically unsaturated monomers (e.g. vinyl acetate, higher vinyl esters, vinyl chloride, ethylene, maleate esters, maleic anhydride, maleimides, acrylonitrile, styrene, acrylamide, N-substituted acrylamides, acrylic esters, methacrylic esters, N-vinylamides, etc.) for the preparation of vinyl resins containing reactive hydroxyl, amine or other functionality. Potential applications for such resins include, for example, protective and decorative coatings, adhesives, hair care and beauty products, paper additives, water treatment polymers, etc.

DETAILED DESCRIPTION OF THE INVENTION

Unsaturated monomers comprising the 3-(N-vinyl-formamido)propionamides and 2-methyl-3-(N-vinylformamido)propionamides are obtained by the reaction of a 3-(N-vinylformamido)propionate or 2-methyl-3-(N-vinyl-formamido)propionate ester with an amine. The materials encompassed by this invention have the general structure:

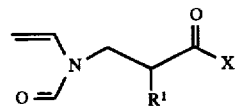

where $R^1$ is hydrogen or methyl;

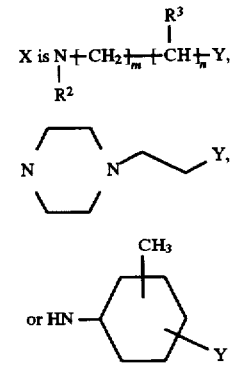

where $R^2$ is hydrogen, methyl, ethyl, 2-aminoethyl, 2-hydroxyethyl, 2-[3-(N-vinylformamidopropionamido] ethyl, or $C_3$–$C_{20}$ alkyl; $R^3$ is hydrogen or methyl; Y is a hydroxyl, amino, alkylamino, alkanol substituted amino, polyalkyleneoxide of one to 30 oxygen atoms, trialkoxysilyl, thiol, urea or substituted urea such as an imidazolidinone, dialkylacetal, piperazine or morpholine ring, 3-(N-vinylformamido)propionamido, or 2-methyl-3-(N-vinylformamido)propionamido group; and m and n are positive integers such that m+n is from 2 to 12. In the case where Y is a polyalkyleneoxide, it may optionally be terminated with OH, O-alkyl, $NH_2$ or 3-(N-vinylformamido) propionamido.

In the preferred embodiment, $R^1$, $R^2$ and $R^3$ are hydrogen, Y is a primary amine, hydroxyl or a second 3-(N-vinylformamido)propionamido group, and m+n=2. Alternatively, X may be derived from a glucosamine, or a hydroxyethylpiperazino, an aminoethylpiperazino or a 3-(N-vinylformamido)propionamidotheylpiperazino group. Also, X may represent a mono- or diaminocyclohexano or alkyl substituted mono- or diaminocyclohexano group with Y equal to $NH_2$, 3-(N-vinylformamido)propionamido, or a 2-methyl-3-(N-vinylformamido)propionamido. The mono-, di-, and tri-3-(N-vinylformamido)propionyl substituted derivatives of diethylenetriamine or higher ethyleneamine condensates are additional possibilities.

The subject compounds are readily prepared by the nucleophilic reaction of certain functional amines with a 3-(N-vinylformamido)propionate or 2-methyl-3-(N-vinylformamido)propionate ester in the presence of a trace quantity of a strongly basic catalyst such as the alkali or alkaline earth metal hydrides or alkali or alkaline earth metal or quaternary amine hydroxides or alkoxides. Bases of the hydride, methoxide, ethoxide, isopropoxide and t-butoxide class are preferred. Sodium hydride and methoxide are especially preferred. Other potentially useful catalysts include the aryl- and alkyllithiums, potassiums and sodiums as well as tertiary amines, amidines, metal amides (e.g. sodium amide), and anhydrous carbonates. The catalyst is present in the reaction mixture in an amount between about 0.0005 and about 5 wt. %, and typically from between 0.05 and 0.7 wt. % based on the total weight of the reactants. Non-fugitive heterogenous basic catalysts, such as phase transfer catalysts or basic exchange resin catalysts are potentially useful in this technology as well.

Synthesis is advantageously performed in a mixture of the neat reactants, however, an inert solvent with a boiling point above 90° C. may also be employed. The amidation reaction is allowed to proceed at a controlled temperature of from about 20° to 170° C. and preferably between 70° to 100° C. The reaction is complete in from about 5 to 180 minutes. The alcohol coproduct of reaction and any residual catalyst may remain in the final product or optionally be removed by some additional purification step or steps such as, for example, solvent washing, distillation, recrystallization, absorption or solvent extraction.

In principle, any 3-(N-vinylformamido)propionate or 2-methyl-3-(N-vinylformamido)propionate can be used as the starting material. In the preferred process, the monomer will be one of the lower alkyl esters, for example, methyl 3-(N-vinylformamido)-propionate or ethyl 3-(N-vinylformamido)propionate. The alcohol coproducts from amidation of these monomers (i.e., methanol and ethanol, respectively) are relatively volatile, thus facilitating removal from the finished product by, for example, distillation at reduced pressure on a wiped film evaporator.

Although a large number of primary and secondary amines are conceivable as coreactants in the amidation of the 3-(N-vinylformamido)propionate esters, it has been found that only certain classes of these materials are sufficiently reactive to be suitable for use in this technology. Suitable coreactants are the linear, cyclic,and branched aliphatic amines in which a terminal functionality, especially an active hydrogen-containing functionality, is located within about 8 carbon atoms of the amide linkage formed. Most preferred are 2-substituted ethylamines in which a terminal amine or hydroxyl functionality is located within two carbon atoms distance of the amide nitrogen. Examples of coreactants conforming to this general description include, but are not limited to, the following: ethylenediamine, 1,2- and 1,3-propanediamine, N,N-dimethylethylenediamine, N,N-dimethyl-1,3-propanediamine, 2-amino-1,3-propanediol, 1,4-diaminobutane, 1,2,4-triaminobutane, 1,4-diamino-2-butanol, diethylenetriamine, N-hydroxyethylethylenediamine, hexamethylenediamine, 2-methyl-1,5-pentanediamine, trimethylolaminomethane, aminoethylpiperizine, aminoethylmorpholine, ethanolamine, and N,N-diethanolamine, glucosamine and N-methylglucosamine, diaminocyclohexane and alkyl substituted diaminocyclohexane, amine capped oligo- or polyethylene or -propylene glycols, such as the Jeffamines, bis(p-aminocyclohexyl)methane, isophoronediamine, and the like, an aminoethyl or aminopropyl urea or substituted urea, such as an imidazolidinone, aminobutyraldehyde dimethylacetal, or aminopropyltrialkoxysilane. Most preferred among these compounds are ethylenediamine and ethanolamine.

In the case where the amidating agent contains two or more primary or secondary amino groups, the molar ratio of the 3-(N-vinylformamido)propionate ester and amine coreactant may be adjusted such that more than one amide bond is formed per amine coreactant, thus yielding a product containing more than one N-vinyl group per molecule. An example of this case is where the 3-(N-vinylformamido) propionate ester is reacted with a diamine in a 2:1 molar ratio to yield a di-3-(N-vinylformamido)-propionamide. In these syntheses, it is preferable that the amine coreactant contain two primary amino groups.

The functional 3-(N-vinylformamido)propionamides are anticipated to have a wide array of uses in free radical polymerization processes and organic syntheses including, but not limited to, the present applications of aminoalkyl and hydroxyalkyl (meth)acrylates and (meth)acrylamides. A particularly useful field of application will be the preparation of resins containing pendant hydroxy or primary amino functionality. For example, 3-N-vinylformamido monomers exhibit superior copolymerizability over acrylic materials in emulsion polymerizations with monomers such as vinyl acetate and ethylene. Thus, in one example of their use, the subject compounds may faciliate the preparation of hydroxy- or primary amino-bearing vinyl acetate/ethylene copolymers. Also, in contrast to primary aminoalkyl acrylate esters, the primary aminoalkyl 3-(N-vinylformamido) propionamides described here exhibit good stability in their free base form due to their reduced tendency to undergo self-Michael addition reactions, or to lose amine titer due to internal transamidations at an ester linkage.

In another specific application of the technology, the reaction product of a 3-(N-vinylformamido)propionate ester with ethanolamine, i.e. 2-hydroxyethyl 3-(N-vinylformamido)propionamide, can be employed as a replacement for 2-hydroxyethyl acrylate in preparation of unsaturated urethane oligomers. For example, 2-hydroxyethyl 3-(N-vinylformamido)propionamide may be reacted with a diisocyanate prepolymer to yield an N-vinyl-terminated resin containing no residual 2-HEA. Such resins may be formulated with less toxic acrylic or other monomers into coatings which are curable under UV light in a manner similar to the commercially available acrylated urethanes referenced above.

In a variation of this application, the N-vinyl oligomers may alternatively be formulated with electron deficient monomers such as maleate esters and/or maleimides into photopolymerizable coatings containing no acrylate species whatsoever. Other examples of such "non-acrylate" radiation-curable systems have garnered commercial interest because of their potential to reduce the health hazards associated with the handling and use of acrylic materials.

The following examples are presented to better illustrate the present invention, and are not meant to be limiting:

EXAMPLE 1

Preparation of N-2-hydroxyethyl 3-(N-vinylformamido)propionamide

Into a 250 mL three neck round bottom flask equipped with a cold water condenser and stirrer was added 28.0 grams (0.459 mol) of ethanolamine, 72.5 grams (0.456 mol) of methyl 3-(N-vinylformamido)propionate, and 0.3 grams of 25% sodium methoxide methanol solution (Aldrich). The mixture was stirred at 90° C. for 20 minutes and then cooled to ambient temperature. The mixture was next placed on a rotary evaporator to remove the generated methanol, yielding 85.0 grams of product as a colorless viscous liquid. Proton NMR analyses indicated a near perfect conversion of the starting materials to the desired 2-hydroxyethyl 3-(N-vinylformamido)propionamide. $^1$H NMR (CDCl$_3$) δ, major rotamer: 2.19 (t, 2H, J=7.5 Hz), 3.04 (bs, 2H), 3.35 (t, 2H, J=5.2 Hz), 3.57 (t, 2H, J=7.8 Hz), 4.04 (bs, 1H), 4.21 (d, 1H, J=9.1 Hz), 4.44 (d, 1H, J=15.7 Hz), 6.35 (d,d, 2H, J=9.2 Hz, J=15.6 Hz), 7.33 (bs, 1H), 8.01 (s, 1H); minor rotamer: most peaks overlapped with peaks of the major rotamer, except, 2.28 (t, 2H, J=6.4 Hz), 4.28 (d, 1 H, J=9.5), 4.40 (d, 1 H, J=16.2 Hz), 6.82 (d, d, 1 H, J=9.4 Hz, J=16.2 Hz), 7.90 (s, 1H). Major/minor rotamer ratio: 70:30.

EXAMPLE 2

Preparation of N,N-di-(2-hydroxyethyl) 3-(N-vinylformamido)propionamide

A 50 mL single-neck round bottom flask equipped with a distillation head was charged with 15.1 grams (0.096 mole) of methyl 3-(N-vinylformamido)propionate, 9.95 grams (0.09 mole) of diethanolamine and 0.15 gram of 25% sodium methoxide in methanol solution. The mixture was stirred at 90° C. for 2 hours and the generated methanol was removed by distillation at reduced pressure. Both proton NMR and GC analyses indicated approximately a 90% conversion to the titled product.

EXAMPLE 3

Preparation of 1,2-di-[3-(N-vinylformamido)propionamido]ethane

The apparatus of Example 2 was charged with 17.1 grams (0.1 mole) of ethyl 3-(N-vinylformamido)propionate, 3.0 grams (0.05 mole) of ethylenediamine and 0.12 gram of 25% sodium methoxide in methanol solution. The mixture was stirred at 90° C. for 3 hours, after which the ethanol coproduct was removed by distillation at reduced pressure. The mixture was then allowed to cool to room temperature yielding the crude product as a yellow solid. NMR analysis of the reaction mixture indicated nearly complete conversion of the ethylenediamine. The solid was recrystallized from toluene/acetone to give pale yellow crystals of 1,2-di-[3-(N-vinylformamido)propionamido]ethane. $^1$H NMR (CDCl$_3$) δ, major rotamer: 2.46 (t, 4H, J=6.2 Hz), 3.30 (bs, 4H), 3.86 (t, 4H, J=7.3 Hz), 4.48 (d, 2H, J=8.7 Hz), 4.70 (d, 2H, J=15.8 Hz), 6.54 (d,d, 2H, J=9.1 Hz, J=15.6 Hz), 6.90 (bs, 2H), 8.25 (d, 2Hz, J=5.6 Hz); minor rotamer: most peaks overlapped with peaks of the major rotamer, except, 6.68 (bs, 2H), 7.13 (d,d, 2H, J=9.3 Hz, J=16.3 Hz), 8.14 (d, 2H, J=5.3 H). Major/minor rotamer ratio: 76:24.

EXAMPLE 4

Preparation of 1,6-di-[3-(N-vinylformamido)propionamido]hexane

The apparatus of Example 2 was charged with 15.7 grams (0.1 mol) of methyl 3-(N-vinylformamido)propionate, 5.8 grams (0.05 mol) of hexamethylenediamine and 0.12 gram of 25% sodium methoxide in methanol solution. The mixture was stirred at 90° C. for 3 hours after which the methanol coproduct was removed by distillation at reduced pressure. The mixture was then allowed to cool to room temperature yielding the product as a yellow solid. NMR analysis indicated about 68% conversion of the starting materials to the desired product.

EXAMPLE 5

Preparation of N-(5-hydroxypentyl)-3-(N-vinylformamido)propionamide

The apparatus of Example 2 was charged with 15.7 grams (0.1 mol) of methyl 3-(N-vinylformamido)propionate, 10.3 grams (0.1 mol) of 5-amino-1-pentanol and 0.12 gram of 25% sodium methoxide in methanol solution. The mixture was stirred at 90° C. for 3 hours after which the methanol coproduct was removed by distillation at reduced pressure. NMR analysis of the remaining amber liquid indicated about 69% conversion to the desired product.

EXAMPLE 6

Synthesis of N-(3,3-Dimethylamino)propyl-3-(N-vinylformamido)propionamide

The apparatus of Example 2 was charged with 15.2 grams (~0.1 mol) of methyl 3-(N-vinylformamido)propionate, 9.9 grams (0.1 mol) of N,N-dimethylaminopropylamine and 0.12 gram of 25% sodium methoxide in methanol solution. The mixture was stirred at 90° C. for 3 hours and generated methanol was removed by distillation at reduced pressure. NMR analysis indicated about 43% conversion to the desired product.

Comparative Examples 7 and 8

The following examples demonstrate the resistance of alkyl 3-(N-vinylformamido)propionates to transesterifcation and to amidation by certain amines.

EXAMPLE 7 (Comparative)

Attempted Synthesis of 2-hydroxyethyl 3-(N-vinylformamido)propionate

The apparatus of Example 2 was charged with 17.1 grams (0.1 mol) of ethyl 3-(N-vinylformamido)propionate, 6.2 grams (0.1 mol) of ethylene glycol, and 0.15 gram of 25% sodium methoxide in methanol solution. The mixture was stirred at 90° C. for 2 hours. No evolution of ethanol was observed during the reaction period. Heating for an additional hour at 135° C. also failed to generate a volatile coproduct which indicated no conversion to the desired product.

EXAMPLE 8 (Comparative)

Attempted Synthesis of N-allyl-3-(N-vinylformamido)propionamide

A 100mL stainless steel high pressure reactor was charged with 17.1 grams (0.1 mol) of ethyl 3-(N-vinylformamido)propionate, 5.7 grams (0.1 mol) of allylamine and 0.15 gram of 25% sodium methoxide in methanol solution. The mixture was heated at 90° C. for 3 hours. Subsequent NMR analysis of the reaction mixture showed no conversion of the starting materials.

EXAMPLE 9

Preparation of Di-{3-(N-vinylformamido) propionamidoethyl}amine

The apparatus of Example 2 was charged with 15.1 grams (~0.096 mol) of methyl 3-(N-vinylformamido)propionate, 9.96 grams (0.0.096 mol) of diethylenetriamine and 0.15 gram of 25% sodium methoxide in methanol solution. The mixture was stirred at 90° C. for 1.5 hours. The generated methanol was removed by distillation at reduced pressure to give a viscouse liquid. GC analysis indicated that about 54.2% of diethylenetriamine and 71.0% of the methyl 3-(N-vinylformamido)propionate were consumed.

EXAMPLE 10

Preparation of Di-{3-(N-vinylformamido) propionamido}methylcyclohexane and 1-[3-(N-vinylformamido)propionamido]-2-amino-methylcyclohexane The apparatus of Example 2 was charged with 15.7 grams (~0.1 mol) of methyl 3-(N-vinylformamido)propionate, 12.8 grams (0.1 mol) of 1,2-diamino-3-methylcyclohexane and 0.10 gram of 25% sodium methoxide in methanol solution. The mixture was stirred at 90° C. for 2 hours and 110° C. for an additional hour. Generated methanol was removed by distillation at reduced pressure to give a viscouse liquid. NMR analysis indicated that about 58.5% of methyl 3-(N-vinylformamido)propionate was consumed.

EXAMPLE 11

Preparation of a Di-N-vinylformamido-terminated urethane resin

A 100 mL round bottom flask equipped with an air cooling condenser was charged with 16.6 grams of N-(2-hydroxyethyl)3-(N-vinylformamido)propionamide from Example 1, 32.3 grams of a diisocyanate-terminated urethane prepolymer (Airthane® XAPC-722, Air Products), 0.12 grams of dibutyl tin dilaurate (T-12®, Air Products), and 12.2 grams of ethyl acetate. The mixture was stirred at 80° C. for about 20 minutes after which the reaction was terminated by removing the reactor from the oil bath and allowing the reactants to cool to room temperature. A sample was withdrawn for IR analysis which indicated a complete loss of the characteristic isocyanate peak at 2270 cm$^{-1}$. The mixture was then placed on a rotary evaporator to remove ethyl acetate, and the desired di-N-vinylformamido terminated urethane resin was recovered as a pale yellow viscous liquid.

EXAMPLE 12

Curing of a Di-N-vinylformamido-terminated urethane resin

The performance of the N-vinyl urethane oligomer prepared in Example 9 in a photopolymerizable composition was assessed in comparison with a commercial acrylated urethane. Standard weight fractions of the oligomer, multi-functional acrylate monomers, reactive diluent, and free radical photoinitiator were prepared according the model formulation below:

| Component | Weight % |
|---|---|
| Urethane di-N-vinylformamide or diacrylate oligomer | 50 |
| TMPTA[1] | 10 |
| TRPGDA[2] | 10 |
| Diluent (NVF or MANVF)[3] | 30 |
| Irgacure ® 184[4] | 2.5 phr (based on wt. of the above) |

[1]Trimethylolpropane triacrylate (UCB Radcure)
[2]Tripropyleneglycol diacrylate (Sartomer SR-306)
[3]N-Vinylformamide or methyl 3-(N-vinylformamido)propionate
[4]1-Hydroxycyclohexyl phenyl ketone (Ciba-Geigy)

The liquid formulations were mixed thoroughly and the Brookfield viscosity was measured before curing. Thin films were drawn down on cleaned 3"×5" aluminum panels using a #10 wire bar. The panels were cured under ultraviolet light in air using a commercial 300 watt/inch medium pressure mercury lamp and conveyor system. Cured film properties were assessed after single and multiple exposures at a conveyor speed of 105 feet per minute. The extent of cure was indicated by measuring the solvent (methyl ethyl ketone) resistance of the films using the double rub test. Film hardness was also noted by the Persoz hardness technique using a BYK Gardner Pendulum Hardness Tester calibrated on glass (412 seconds).

Table 1 compares the properties of the formulations containing the di-N-vinylformamido-terminated urethane oligomer (NVFTO) and a commercial urethane diacrylate oligomer (ATO) with different monofunctional diluent monomers. As can be seen from the data, the N-vinyl oligomer cured rapidly to give chemically-resistant crosslinked films that exhibited good gloss. In fact, the performance and properties of the NVFTO formulations were at least as good as, and in most instances superior to, the ATO formulations, without the disadvantage of the toxicity problems associated with the commercial ATO formulations.

TABLE 1

| Oligomer Diluent | NVFTO NVF | NVFTO NVF | NVFTO MANVF | NVFTO MANVF | ATO MANVF |
|---|---|---|---|---|---|
| Formulation viscosity (cps, 25° C.) | 390 | 390 | 720 | 720 | 1700 |
| Film thickness (μ) | 3.1 | 4.0 | 4.0 | 3.8 | 4.0 |
| # Passes @ 105 fpm | 1 | 4 | 1 | 4 | 2 |
| Persoz hardness (seconds) | 38 | 109 | 68 | 64 | 38 |
| Gloss (60°) | 99.7 | 98.2 | 99.0 | 99.6 | 99.7 |
| # MEK double rubs | >200 | >200 | >200 | >200 | >200 |

Having thus described the present invention, what is now deemed appropriate for Letters Patent is set out in the following appended Claims.

We claim:

1. N-vinyl compositions corresponding to the general structural formula:

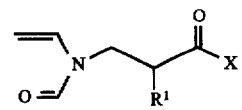

where $R^1$ is hydrogen or methyl;

X is diaminomethyl cyclohexane, aminomethyl cyclohexane or

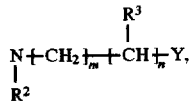

where $R^2$ is hydrogen, methyl, ethyl, 2-aminoethyl, 2-hydroxyethyl, 2-[3-(N-vinylformamido-propionamido]ethyl, or $C_3$–$C_{20}$ alkyl; $R^3$ is hydrogen or methyl; Y is a hydroxyl, amino, alkylamino, alkanol substituted amino, 3-(N-vinylformamido) propionamido, or 2-methyl-3-(N-vinylformamido) propionamido group; and m and n are positive integers such that m+n is from 2 to 12.

2. A composition in accordance with claim 1 wherein $R^1$ is hydrogen.

3. A composition in accordance with claim 2 wherein both m and n are 1.

4. A composition in accordance with claim 3 wherein $R^3$ is hydrogen.

5. A composition in accordance with claim 2 wherein Y is a 3-(N-vinylformamido)-propionamido group.

6. A composition in accordance with claim 2 wherein Y is hydroxyl.

7. A composition in accordance with claim 1 wherein $R^2$ is a 2-hydroxyethyl group.

8. A composition in accordance with claim 1 wherein Y is $NH_2$.

9. A composition in accordance with claim 2 wherein $R^2$ is hydrogen.

10. A composition in accordance with claim 1 wherein alkanol substituted amino is 2-hydroxyethylamino or 2- or 3-hydroxypropylamino.

* * * * *